United States Patent [19]

Pieniak

[11] 4,300,562
[45] Nov. 17, 1981

[54] LAMINATED STRUCTURES HAVING GATHERED MARGINAL PORTIONS

[75] Inventor: Heinz A. Pieniak, Chicago, Ill.

[73] Assignee: Johnson & Johnson Baby Products Company, New Brunswick, N.J.

[21] Appl. No.: 120,195

[22] Filed: Feb. 11, 1980

[51] Int. Cl.³ .................. A41B 13/02; A41B 7/00
[52] U.S. Cl. ........................... 128/287; 2/237; 2/401; 428/194
[58] Field of Search .............. 128/284, 286, 287, 288; 2/76, 78 C, 123, 221, 401, 237, DIG. 7; 428/12, 61, 167, 194, 231, 247

[56] References Cited

U.S. PATENT DOCUMENTS

| | | |
|---|---|---|
| 1,544,312 | 6/1925 | Gray ........................................ 2/237 |
| 2,838,047 | 6/1958 | Sidnell .................................. 128/288 |
| 2,957,792 | 10/1960 | Magid .................................. 428/194 |
| 3,842,438 | 10/1974 | Campbell, Jr. et al. ................. 2/237 |
| 4,067,337 | 1/1978 | Ness ..................................... 128/284 |
| 4,069,822 | 1/1978 | Buell .................................... 128/284 |
| 4,182,334 | 1/1980 | Johnson ............................... 128/284 |
| 4,210,143 | 7/1980 | Jonckheere ......................... 128/287 |

Primary Examiner—C. Fred Rosenbaum
Attorney, Agent, or Firm—Robert L. Minier; Martha A. Michaels

[57] ABSTRACT

A laminated structure having a gathered marginal area which provides an improved fit about a portion of the human body, said laminated structure comprising an elastic member disposed between first and second substrates of flexible gatherable material, said elastic member comprising a plurality of interconnected longitudinally extending elastic elements defining apertures therebetween, the longitudinally extending elements having different cross-sectional areas to provide varying degrees of tension across the width of the marginal area and the first and second substrates of said laminated structure being secured together through at least some of said apertures.

29 Claims, 12 Drawing Figures

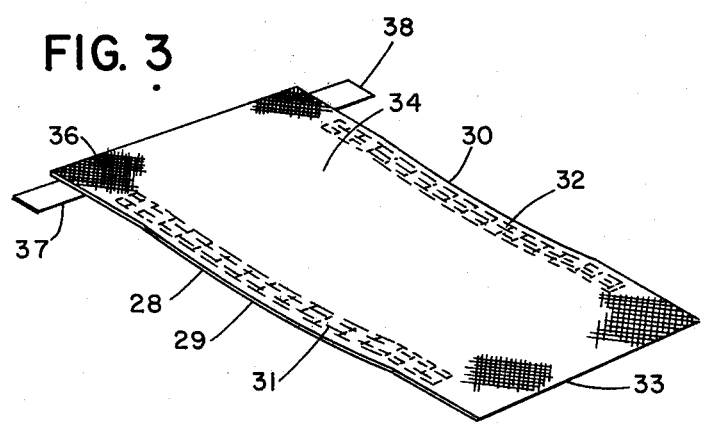
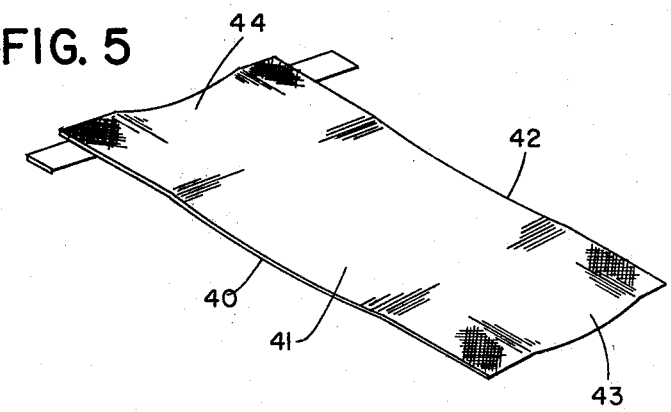

FIG. 6
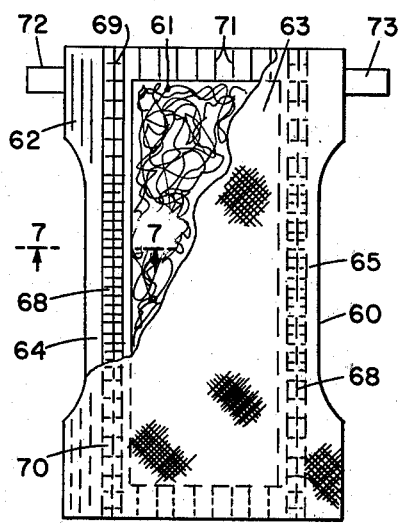
FIG. 8
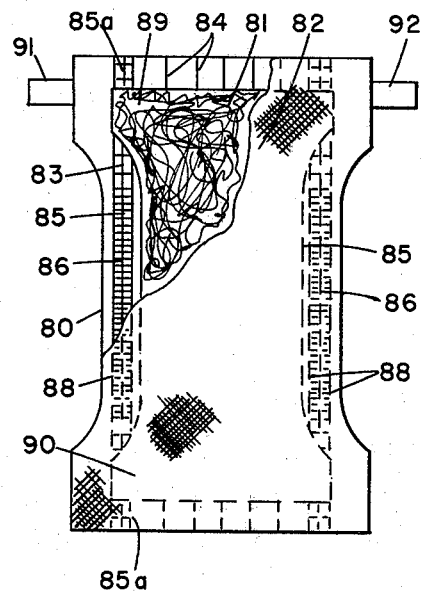
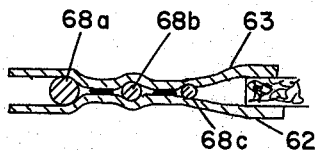
FIG. 7

LAMINATED STRUCTURES HAVING GATHERED MARGINAL PORTIONS

BACKGROUND OF THE INVENTION

Recent years have seen an increased demand for inexpensive apparel and the development of new and inexpensive components of construction and methods of construction of articles of apparel. In certain instances, there is a demand for apparel that is very inexpensive and, indeed, disposable. New elastomeric materials and methods of incorporating them into portions of a garment have been developed to meet the desire to fit these types of garments to a human form. For example, U.S. Pat. No. 3,639,917 discloses the use of a strip of a heat recoverable elastomeric material to gather the cuff of a disposable hospital gown.

Disposable diapers have been marketed which include an elastic or stretch member in the longitudinal side edges of the disposable diaper to provide elasticity about the leg of the infant when the diaper is applied. Examples of such stretchable fitted diapers which have elastic members disposed in the longitudinal side edges of the diaper are shown in U.S. Pat. Nos. 3,860,003 and 4,050,462. By being able to elastically contract the longitudinal sides of the diaper which are the leg and thigh encircling portion of the diaper once placed on an infant, you can compress the diaper about the leg of the infant. By virtue of this compressing, you reduce leakage at the leg of the infant and the tighter you make the fit, the more you tend to reduce leakage. However, if the fit is too tight, you will cause irritation on this tender portion of the thigh, especially when the diaper is wet. There are also a number of patents which disclose means for making the waist encircling portion of a disposable diaper elastic for tighter fit of the diaper about the waist of the wearer, for example, as shown and described in U.S. Pat. Nos. 3,995,637 and 3,995,640. Disposable diapers usually comprise a facing and a backing layer which are substantially co-extensive and a somewhat smaller absorbent core or panel interposed between the facing and backing layer. The facing and backing layers are adhered together about their perimeter by hot melt adhesive or other adhesive material as is well known. In producing stretch or elastic diapers, an elastic member in its stretched or partially stretched state, is interposed between the facing and backing sheets along one or more edges of the diaper. The elastic member is adhered either to the facing and/or the backing sheets by adhesive or similar means and allowed to relax to produce elastic sections at the edges of the diaper. An example of a method for inserting elastic members in disposable diapers is disclosed in U.S. Pat. No. 4,081,301.

The incorporation of these elastic members into disposable diapers has increased both the cost of materials used in the diaper and the cost of construction of disposable diapers. With solid elastic members, it is necessary to adhere the side edges of the facing and backing sheets together, either directly or by their mutual attachment to the elastic member.

When adhesively securing such an elastic member into a disposable diaper, the adhesive chosen must be elastomeric or must be applied in a discontinuous pattern or the glue may make the diaper too stiff to gather.

In commonly assigned co-pending patent application, Ser. No. 60,704 filed July 25, 1979, there is disclosed apertured elastic members which have substantial advantages over other types of elastic members in that they are simpler and more economical to insert and function very well by providing a good fit with a minimum of irritation. The present invention is an improvement on such apertured elastic members.

The laminated structures of the present invention provide improved fit about the portion of the human body to which they are applied. In the various parts of the extremities of the human body, such as the wrist, thigh, etc., the circumference of the extremity increases as you move along that extremity towards the body torso. Therefore, an elastic of any width will apply different forces on that extremity with the most force and the primary seal usually being at the contact line between the elastic and the body part having the greatest circumference.

Contrasted to the above, the apertured elastic member used in the laminated structures of the present invention has a varying degree of tension across its width and can be used to apply uniform forces about and along the extremity or even to apply the greatest force at the contact line between the elastic and the body part having the least circumference. The laminated structures of the present invention provide not only an improved fit but unexpectedly improve sealing capabilities with a minimum of irritation.

SUMMARY OF THE INVENTION

What I have discovered is an improved laminated structure having a marginal area with a gathered portion which provides improved fit about a portion of a human body. The laminated structure comprises first and second substrates of flexible, gatherable material and an elastic member disposed between the substrates in the marginal area thereof. The elastic member comprises a plurality of interconnected longitudinally extending elastic elements. The longitudinal elements have different cross-sectional areas to provide varying degrees of tension across the width of the marginal area. The first and second substrates are secured together through at least some of the apertures.

The cross-sectional areas may vary quite widely across the width of the elastic member. However, the degree of taper in most body extremities is quite gradual and, hence, large variations in the cross-sectional areas is not required for most end uses. Theoretically, the elastic force applied is directly proportional to the cross-sectional area; i.e., as the area is increased, the force applied will also increase in a proportional relationship. In practice, this is not exactly the case as the materials to which the elastic member is laminated do have some effect on the elastic member and the force to area relationship. In the elastic member of the present invention, individual longitudinally extending elements may have a cross-sectional area of from about 0.00001 sq. inches to about 0.0025 sq. inches and preferably from about 0.00005 to 0.0005 sq. inches.

The laminated structure of the present invention may be used in any fitted garment but perhaps is most suited for use in inexpensive and disposable apparel. The laminated structure can be incorporated into the sleeve cuff, the leg encircling portion, about the neck, and the waist of an article of apparel. In particular, the laminated structure may be incorporated into both the waist and thigh encircling portions of a disposable diaper or other disposable undergarments. The improved laminated structure of the present invention reduces the pressure applied to the skin of the wearer and, in a disposable diaper or a disposable undergarment reduces the possibility of irritation and rash when wet. The laminated structure of the present invention may also be used in such products as elastic bandages, fitted tableclothes, nursing pads, and the like.

The laminated structures of the present invention may be readily produced by inserting the described elastic members in a stretched condition between first and second substrates and these substrates adhered together between some of the openings in the elastic member to hold the elastic member in place. If desired, the elastic member may be held in place over only a portion of its length and may then be severed in portions not held in place and allowed to relax and contract in such unheld portion.

The elastic member has a width of from about ¼ inch to about 2 inches and the member may have a thickness of from 1 to 50 mils and preferably from about 5 to 20 mils. The elastic member may be made of any of the standard film materials which are stretchable and are recoverable and have a modulus of elasticity at 100 percent elongation of from about 20 to 2000 lbs./sq. inch. In a disposable diaper in accordance with the present invention, the elastic member may be disposed between the backing and facing sheet of the diaper in the longitudinal side margins of the diaper.

It should be pointed out that by using the elastic members in accordance with the present invention, the insertion of the member into the product and the adherence thereto is greatly simplified and, hence, has considerable economic benefit in the manufacturing process. The apertured portion insures a uniform, intermittent lamination between the elastic and non elastic layers and reduces the criticality of adhesive application. Also, the apertures combined with adhesion of the layers through these apertures provides that the final lamination acts or performs in its stretch, recovery and similar elastic properties substantially the same as the original elastic member, thus allowing for greater certainty in predicting the quality and functionality of the final product.

BRIEF DESCRIPTION OF THE DRAWINGS

In the Drawings:

FIG. 3 is a perspective view illustrating a disposable diaper in accordance with the present invention, with the diaper laid out flat;

FIG. 5 is a perspective view of another embodiment of the disposable diaper embodying the present invention;

FIG. 6 is a plan view of one embodiment of the disposable diaper of this invention with a portion broken away to show interior detail;

FIG. 7 is an enlarged cross-sectional view taken along line 7 7 of FIG. 6;

FIG. 8 is a plan view of another embodiment of the disposable diaper of this invention with a portion broken away to show interior detail;

DESCRIPTION OF THE PREFERRED EMBODIMENTS

For a laminated structure of the present invention, the elastic member is a readily stretchable, preferably thermoplastic member that possesses a certain minimum elastic recovery.

The term "elastic" as used herein, refers to sheets, films, ribbons, filaments, and the like which have a recovery of at least 90 percent, when elongated to within 10 percent of their field point and measured in accordance with the following formula:

$$\text{Percent retraction} = (L_e - L_t)/(L_e - L_o) \times 100$$

where;

$L_o$ = original length of sample
$L_e$ = fully extended length
$L_t$ = length of sample measured three seconds after release from extended length The thickness of the elastic member may be from about 1 to 50 mils and is preferably from about 5 to 20 mils. They have a width of from ¼ inch to 2 inches and preferably in diaper applications widths of from ½ inch to 1 inch have been found satisfactory. For ease of stretchability, the moduls of elasticity of the elastic member at 100 percent elongation should not exceed about 2000 lbs./sq. inch. The modulus of elasticity is preferably substantially less than 2000 lbs./sq. inch, and most preferably is about 75 to about 400 lbs./sq. inch.

Figure 1:
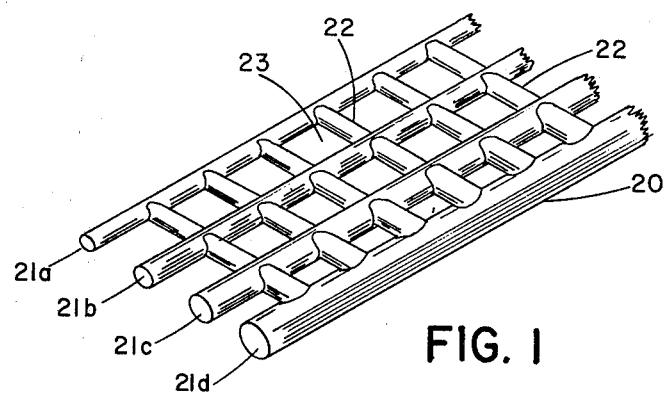
FIG. 1 is an enlarged perspective view illustrating an elastic member which may be used in accordance with the present invention.

As shown in FIG. 1, the elastic member 20 useful in accordance with the present invention comprises a plurality of longitudinally extending elastic elements 21a, 21b, 21c and 21d. These elements are transversely connected by elements 22. The transversely connecting elements 22 may or may not be elastic. However, as will be hereinafter described, the elastic members are preferably made from a single component and, hence, the properties of the member are substantially uniform throughout the member. The openings 23 in the elastic members may have any shape such as square, oval, round, rectangular, or the like. Either square or rectangular shaped openings are preferred with the longitudinal and transverse elements perpendicular to each other. This configuration virtually eliminates any "necking down", reduction in the transverse dimension when the member is stretched longitudinally, and hence, facilitates insertion of the member with the product and the adhesion of the layers of the laminate through the openings in the elastic member. Depending on the modulus of elasticity of the material used and the thickness and width of the member, the number of openings in the elastic member may vary from 2 to 100 openings per linear inch in both the longitudinal and transverse direction of the member. In addition, the spacing between the elastic elements may vary from the transverse to the longitudinal direction.

The cross-sectional areas of the longitudinally extending elements may be varied across the width of the marginal area so that the outermost longitudinally extending elastic elements has the largest cross-sectional area while the innermost longitudinally extending element has the smallest cross-sectional area. The longitudinally extending element between the outermost and innermost elements are substantially uniformly decreased in cross-sectional area from the outermost element to the innermost element. A structure such as that described allows for a uniform application of pressure about a tapered body portion with the longitudinally extending element having the largest cross-sectional area being positioned so as to contact the smallest circumference of the tapered body to which the structure is applied. Such construction also provides for an excellent seal about the body portion in that the seal is uniform over the width of the elastic member as compared to prior art seals where that seal is substantially at a line about the body. In another embodiment of the laminated structure of the present invention, the elastic member comprises a plurality of longitudinally extending elastic elements in the side marginal area with the longitudinally extending elements in the second portion of the margin having the largest cross-sectional area while the longitudinally extending element at the innermost and at the outermost edges of the margin having smaller cross-sectional areas. I have found cross-sectional areas in the individual longitudinally extending elements of from 0.0001 sq. inches to about 0.0025 sq. inches to be satisfactory; however, my preferred range is from 0.00005 sq. inches to 0.0005 sq. inches. Of course, this will vary depending on whether the structure is to be used on the wrist or leg of an adult or on the wrist or leg of an infant.

As shown in FIG. 1, the longitudinally extending elastic elements 21a, b, c, and d have different cross-sectional areas with 21a having the smallest cross-sectional area, 21b the next smallest, 21c the next smallest, and 21d the largest cross-sectional area. This varying cross-sectional allows for a varying tension to be applied by the elastic member when used.

Figure 2:
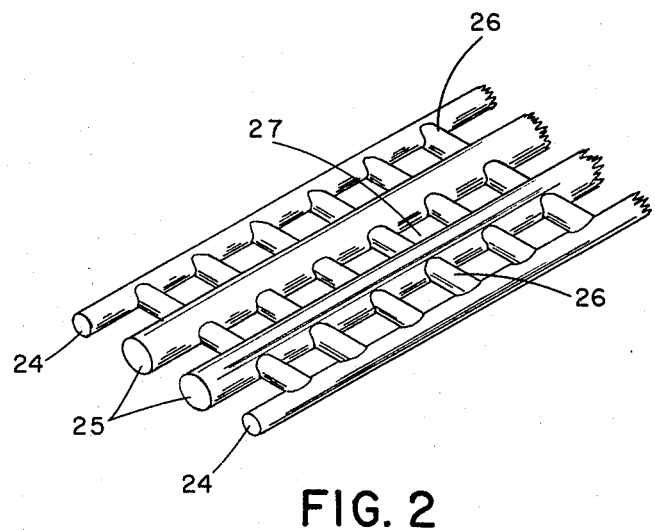
FIG. 2 is an enlarged perspective view illustrating another embodiment of an elastic member which may be used in accordance with the present invention.

Referring to FIG. 2, there is shown another embodiment of an elastic member in accordance with the present invention. In this embodiment, longitudinally extending elastic members 24 and 25 are transversely connected by elements 26 to define openings 27 therebetween. The outer longitudinally extending elastic elements 24 have smaller cross-sectional areas then the two inner longitudinally extending elements 25 to provide varying tension across the width of the elastic member.

It should be pointed out that though I have shown both the longitudinal and transversely extending elements as circular in shape, either or both of them may have other cross-sectional shapes such as oval, elliptical, square, rectangular or other geometric shapes.

Figure 4:
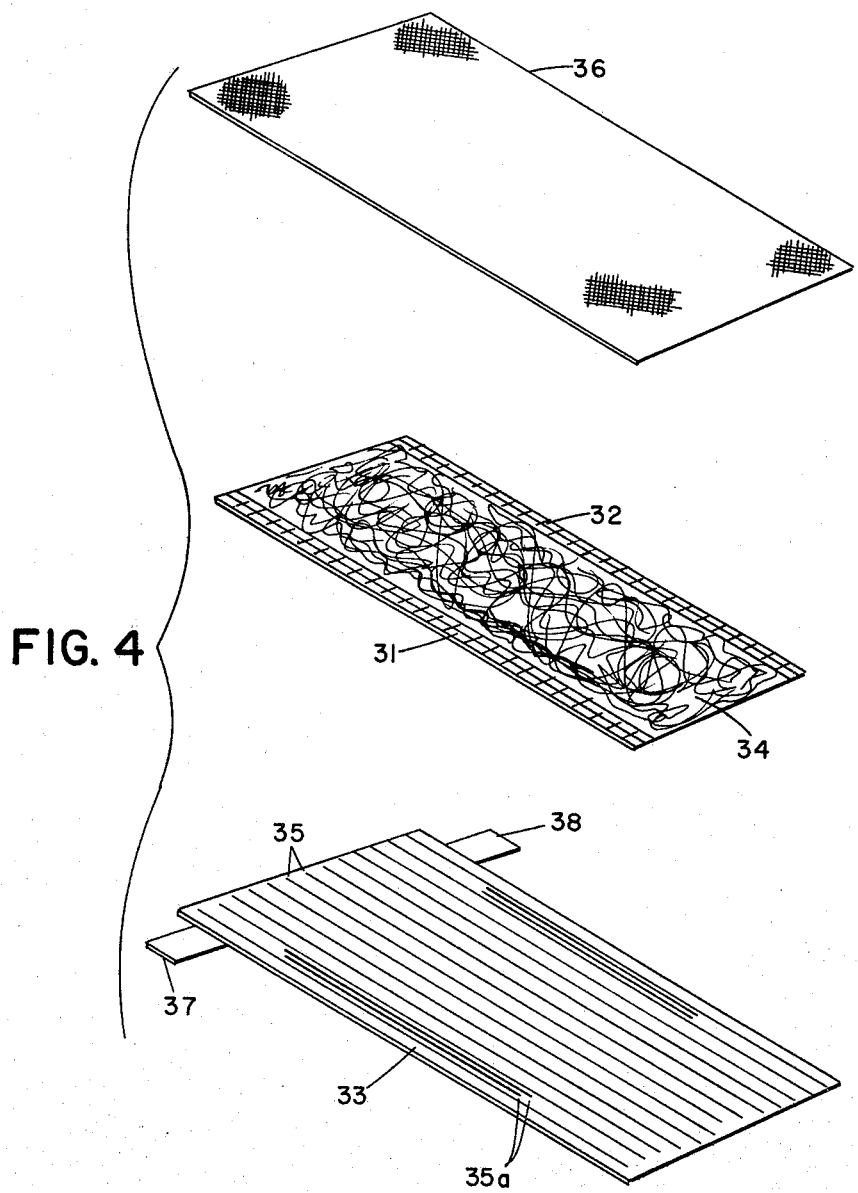
FIG. 4 is an exploded perspective view showing relative positioning of the diaper elements depicted in FIG. 2.

Referring to FIG. 3, a disposable diaper 28 embodying the present invention has longitudinal side margins 29 and 30. The central portion of each side margin is gathered to provide improved fit about the baby's thighs. The elastic member 31 and 32 in each of the longitudinal side margins is an elastic member according to the present invention. Individual components of the disposable diaper of FIG. 3 are illustrated in FIG. 4. The diaper additionally includes a first layer or backing layer 33 made of a moisture-impermeable material, a rectangular absorbent batt 34 superimposed over backing layer 33 and secured thereto by a series of glue lines 35 deposited on the backing layer, and a second layer or facing layer 36 made of a moisture-permeable web and positioned in super imposed relationship to the absorbent batt. The absorbent batt is of smaller area than the backing and when substantially centered on the backing, is spaced from the longitudinal sides as well as the transverse ends of the diaper. The absorbent batt is flanked on its longitudinal sides by elastic members 31 and 32 located generally parallel the longitudinal edges of the batt and which, in an extended state, are secured between the backing and the facing by means of the adhesive lines 35a. A moisture-pervious facing 36 is superimposed over the absorbent batt and secured to the backing by means of the end and side portions of the glue lines 35. The facing is also secured to the backing between the openings in the elastic member by adhesive lines 35a. For securing the diaper about a baby, the diaper is provided with pressure-sensitive tape tab members 37 and 38.

In the manufacture of the diaper, only the central portions of the elastic members 31 and 32 act to gather the longitudinal side margins of the diaper. The end portions of the elastic members merely "snap back" to a relaxed, unstretched state and do not act to gather the diaper.

Another method of manufacturing the disposable diaper of the present invention, when using thermoplastic elastic members, is to adhere the elastic member between the facing and backing layers along the entire longitudinal edge of the diaper. Thereafter, the portions of the elastic member which is desired not act to gather the diaper are rendered inelastic by applying heat to that portion of the member and remove its elasticity.

The elastic member of the present invention may be produced by a variety of methods such as passing an appropriate stretchable and recoverable film between the nip of a pattern forming roll and a back-up roll in a procedure analogous to that shown in U.S. Pat. Nos. 3,881,381 and 3,632,269. When using such a procedure, the pattern of the forming roll should be altered to provide for the varying cross-sectional areas of the longitudinally extending elements.

FIG. 5 shows another disposable diaper 40 similar to that shown in FIG. 3 with the exception that all four edge portions; that is, the two longitudinal side margins 41 and 42 and the front 43 and rear 44 end portions are elastic members in accordance with the present invention inserted between the facing and the backing with the central portions thereof elastic.

In the embodiment shown in FIG. 6, a disposable diaper 60 is provided with a substantially rectangular panel 61 sandwiched between a backing 62 and facing 63 and together with the backing and facing define side margins 64 and 65. Curvilinear cut-outs are provided in the respective central side portions of the facing and backing for further fit enhancement. Pre-stretched elastic members 68 are positioned in the longitudinal side margins and are secured between the backing and facing along the longitudinal sides of the absorbent panel. The elastic members have been heated and rendered inelastic at end positions 69 and 70. Glue lines 71 secure the facing and absorbent panel to the backing and adhesive tape tabs 72 and 73 provide diaper securement means.

Referring to FIG. 7, which is a cross-sectional view taken along 7-7 of FIG. 6, there is shown the impervious backing member 62 with the elastic member 68 secured between the backing member and the facing member 63 by the glue lines.

The longitudinally extending elements 68a, b, and c have varying cross-sectional areas with elements 68a having the largest cross-sectional area and element 68c the smallest cross-sectional area.

In the embodiment shown in FIG. 8, the disposable diaper 80 is provided with an absorbent batt 81 and also having curvilinear side cut-outs and sandwiched between facing 82 and backing 83 having similar cut-outs. Glue lines 84 serve to secure the batt and facing to the backing. Elastic members 85 are situated in the general rectilinear diaper side margins. The elastic members are secured between the facing and backing at the central portion 86 by adhesive lines 88 which may be applied at the same time as, and may lie along the same line as certain of the glue lines 84.

Protruding portions 89 and 90 of the absorbent batt overlap into the four corners of the diaper.

In the manufacture of this diaper, the elastic members are positioned on top of the protruding portions. The end portions 85a of the elastic member are heated and rendered inelastic causing the elastic member to break over the protruding portions as shown.

The varying cross-sectional area elastic members of the present invention are especially adaptable for use with different shapes of diapers. For example, the elastic member of the present invention provides an excellent fit in diapers with facing and backing members having shallow cut-outs combined with much deeper cut-outs or shaping of the absorbent panel.

The varying cross-sectional area elastic members of the present invention are also very suitable for use in the waistband area of diapers or other waist encircling garments. Garment and diaper waistbands tend to roll or fold over when the garment is being worn. My new elastic member disposed in the waistband of a garment will readily eliminate such rolling or folding over.

The elastic member suitable for use in the diapers contemplated may be made from films extruded, calendered, or otherwise formed to the desired thickness and pattern of openings utilizing low stretch modulus materials made from any rubbery elastic material. Specifically unvulcanized thermoplastic compositions which are made of an elastomeric component and an optional compatible modifier which is a thermoplastic polymer of a relatively low molecular weight but solid at ambient temperatures have been found to make suitable elastic members for use in accordance with the present invention.

Illustrative of the elastomeric components suitable for present purposes are block copolymers which comprise terminal thermoplastic polymer blocks and at least some non-terminal or intermediate elastomeric polymer blocks. Block copolymers of this general type may be prepared using a step-wise polymerization initiator; e.g., an organolithium compound. Such block polymerization techniques are well known in the art.

The elastic component can be linear or radial $A^1$-B-A block copolymers of mixtures thereof with simple $A^1$-B block copolymers wherein $A^1$ and $A^2$ can be alike or different and represent a thermoplastic polymer block, such as poly (vinyl arene) block, and B represents an elastomeric polymer block such as a conjugated diene or a lower (i.e., $C_1$-$C_4$) alkene. The modifier component is a low molecular weight thermoplastic polymer having an average molecular weight of about 500 to 7,500 and is present in the composition in an amount of about zero to about 200 parts by weight per 100 parts by weight of the elastomeric component.

A preferred thermoplastic film composition for the elastic member comprises an elastomeric component which contains, as a major constituent thereof, an unvalcanized linear block copolymer of the general configuration;

$A^1$-B-$A^2$ wherein $A^1$, $A^2$ and B have the same meaning as hereinabove. In these block copolymers, the A-blocks are derived from styrene or styrene homologues, and the Bblocks are derived from conjugated dienes or lower alkenes. The thermoplastic polymer modifier is compatible with the elastomeric component and associates principally with the thermoplastic terminal blocks of the aforesaid unvulcanized block copolymer. The thermoplastic polymer modifier preferably has an average molecular weight of about 1000 to about 3000, and is present in the film composition in an amount of about 80 to 200 parts by weight per 100 parts by weight of the elastomeric component.

The preferred $A^1$-B-$A^2$ block copolymers have A-blocks derived; i.e., polymerized or copolymerized, from styrene or styrene homologues; and B-blocks derived from conjugated dienes, such as isoprene or butadiene, or from lower alkenes such as etylene and butylene. Small proportions of other monomers also may enter into the block copolymers themselves. The individual A-blocks can have an average molecular weight of at least about 6000, preferably in the range of about 8000–30,000, and the A-blocks constitute about 5—50 percent, preferably about 10—30 percent, by weight of the block copolymer. The average molecular weight of the B-blocks for linear $A^1$-B-$A^2$ block copolymers preferably is in the range of about 45,000–180,000 and that of the linear copolymer, itself, preferably is in the range of about 75,000–200,000. The average molecular weight of the radial $A^1$-B-$A^2$ block copolymers preferably is in the range of about 125,000–400,000. The term "linear block copolymer" (or copolymers) includes branched $A^1$-B-$A^2$ copolymers as well as unbranched $A^1$-B-$A^2$ copolymers. The radial $A^1$-B-$A^2$ copolymers useful for manufacture of elastic members for diapers of this invention are of the type described in United States Letters Pat. No. 3,281,383 to Zelinski, et al. and conform to the following general formula: $(A-B_n-X)$, wherein A is a thermoplastic block polymerized from styrene or styrene homologues, B is an elastomeric block derived from conjugated dienes or lower alkenes, as indicated above, X is an organic or inorganic connecting molecule, with a functionality of about two to four as described in U.S. Pat. No. 3,281,383, or possibly with a higher functionality as described in the Article entitled "New Rubber Is Backed By Stars" appearing on Page 35 of the June 11, 1975, issue of *Chemical Week*. As used hereinabove, "n" has a value corresponding to the functionality of X.

The preferred elastic member is highly thermoplastic and, though elastomeric, is unlike rubber in that it exhibits a relatively sharp melting point and is capable of being heat shaped. Also, the elastic member can form permanent heat seals to substrates such as non-woven fabrics or the like, at relatively low heat sealing temperatures, generally not above about 350° F. The member is very flexible, extensive and soft, and normally exhibits a Gurley stiffness of about one or less at a film thickness of one mil.

Elastic members especially suitable for use in disposable diapers may be made from combinations of thermoplastic rubber and amorphous polypropylene. The thermoplastic rubbers used in such combinations are block copolymers having blocks of polybutadiene or polyisoprene, and blocks of polystyrene. A review article discussing these materials is "Structure and Properties of Block Polymers And Multi-phase Polymer Systems: An Overview of Present Status and Future Potential", by S. L. Aggarwal, Polymer, Vol. 17, November 1976, Pages 938–956. Two representative types of thermoplastic rubbers useful in these combinations are the linear block copolymers (A-B-A) having a mid-block of polybutadiene or polyisoprene and end-blocks of polystyrene, and the "star" or "radial" block copolymers having from 4 to 20 "arms" connected to a common center. Each arm is an A-B block copolymer, the inner portion being polybutadiene or polyisoprene, with the outer portion being polystyrene.

The material added or combined with the thermoplastic rubber, primarily to improve processability, while still retaining the characteristic rubbery properties of the rubber, is amorphous polypropylene. Amorphous polypropylene is a known material. It is essentially atactic polypropylene having an isotactic content of not more than about 20 weight percent, and preferably not more than about 10 weight percent.

The amorphous polypropylene is employed in an amount sufficient to improve the processability of the thermoplastic rubber when extruding thin films or sheets. The exact minimum amount of amorphous polypropylene which must be employed varies somewhat from case to case, but it is usually of the order of about 10 weight percent, based on weight or rubber plus amorphous polypropylene, although the proportion may be as low as about 5 weight percent (on the same basis) in some cases. The upper limit of polypropylene will also vary from case to case, depending on the nature of the ingredients and the use intended for the product. At proportions above about 35 weight percent (on the same basis) a significant reduction in the characteristic rubbery elastomeric properties of the product begin to occur. This may be acceptable for some uses, and not for others. Thus, the upper limit of amorphous polypropylene would be that point at which the product still retains significant rubber elastomeric characteristics.

Other conventional materials, employed in the usual amounts, can be employed in the mixture for their known purposes. Such materials include pigments, anti blocking agents, stabilizers, anti-oxidants, ultraviolet stabilizers, bonding aid, and the like.

In some embodiments of the disposable diaper of the present invention, the elastic member is a member which may be made elastic by imparting heat or other forms of energy to the member to shrink the member and provide it with elastic characteristics.

The heat shrinkable reticulated films which may be used as elastic members in the disposable diapers of the present invention may be the polyolefin films which have been oriented to a degree and which will then become elastic when heat shrunk. Usually, a preferred technique for orienting the polyethylene film to provide the heat shrunk elastic properties is by irradiation such as suggested in British Pat. No. 866,820. Also, useful as the heat shrunk elastic members are the copolymers of ethylene and vinyl acetate, ethylene and ethyl acrylate, and the like. The forming of such copolymers is well known and specific methods of forming such materials are disclosed in U.S. Pat. Nos. 2,200,429 and 2,953,551. After the copolymer is formed and made into a film, it is given the proper orientation as described in the previously mentioned British Pat. No. 866,820.

The elastic member useful in accordance with the present invention may also be made from other materials; such as, natural rubber, the synthetic rubbers, and the like.

Broadly, the elastic members may be made from materials having elongations of from 20 to 1000 percent and preferably from about 50 to 500 percent with recoveries in the range of 20 to 100 percent and preferably from 70 to 100 percent. The material should have a force to stretch it 100 percent of from 30 to 2000 grams.

The important factor to remember is that when the material is placed in the end product, the material be elastic, as previously defined, so it functions as such an elastic in the final product. For example, in the diaper leg band area, the member should have 90 percent or better recovery in very short periods of time and preferably almost instantaneously the member should also require a relatively low amount of force to stretch the leg band area back to its original or non-gathered length. Such force should be less than 200 grams and may be as low as 20 grams.

Figure 9:
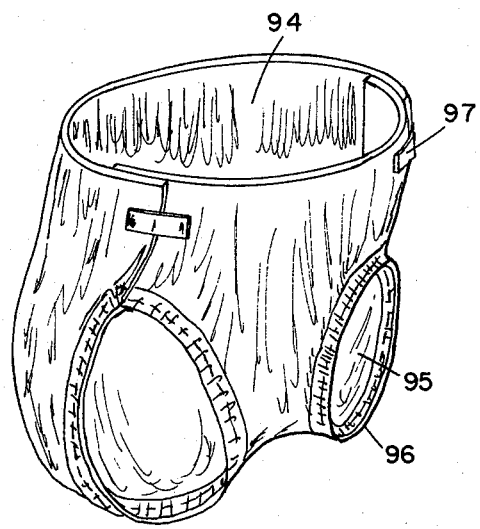
FIG. 9 is a perspective view of a disposable diaper according to the present invention viewed in the configuration it assumes when disposed about a wearer.

FIG. 9 illustrates a diaper 94 in accordance with the present invention in the configuration it takes when placed on the body of a wearer. The leg encircling portions 95 of the diaper have differential elasticity with the outer edge 96 of the opening having a greater elastic force than the inner portion of the opening. The diaper is secured about the wearer by the tape tabs 97.

Figures 10, 11:
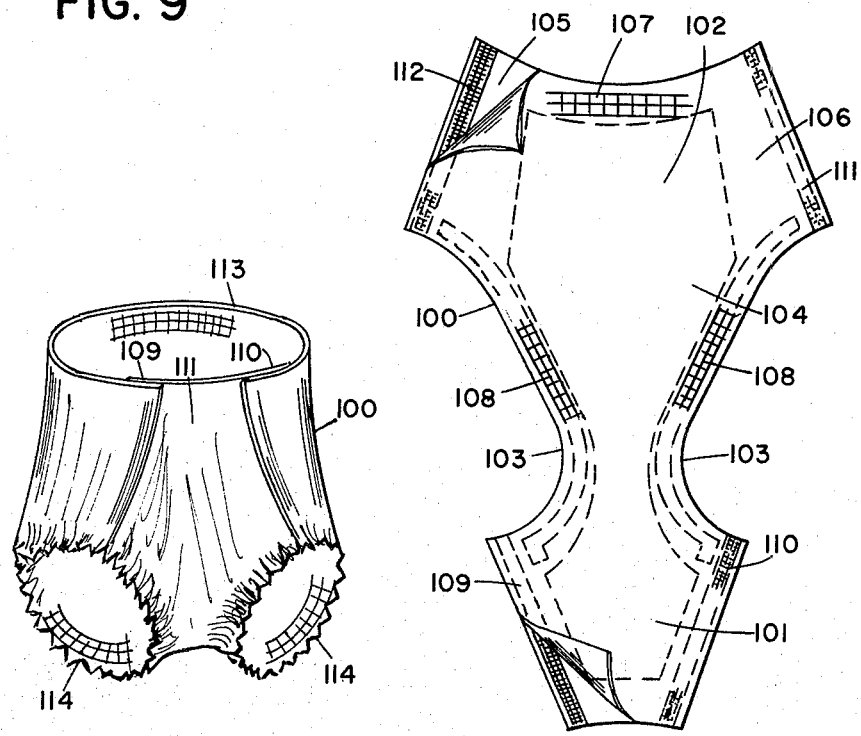
FIG. 10 is a plan view of a disposable undergarment laid out flat, in accordance with the present invention with portions folded back to show interior detail.
FIG. 11 is a perspective view of the disposable undergarment of FIG. 9 viewed in the configuration it assumes when disposed about a wearer.

FIG. 10 illustrates a disposable undergarment 100 suitable for use in toilet training infants, or by incontinent children or adults. The undergarment has a front portion 101, a rear portion 102, and a crotch portion 103 comprised of an intermediate liquid absorbent panel 104 disposed between outer layer 105 and a moisture-permeable inner layer 106. The waistband of the undergarment may be gathered by an elastic member 107 located between the ends of the inner and outer layers at the rear portion and optionally between the ends of the inner and outer layers at the front portion. The longitudinally extending elements of this elastic member may all have the same cross-sectional areas. The undergarment is also provided with elastic members 108 disposed between the inner and outer layers at the side margins of the crotch region. The longitudinally extending elements of these elastic members having varying cross sectional areas with the outermost elements having the largest cross-sectional area.

FIG. 11 illustrates the disposable undergarment 100 of FIG. 10 about a wearer in use; both side margins 109 and 110 of the front portion being joined to respective side margins 111 and 112 of the rear portion to define a waist portion 113 and self-fitting leg apertures 114.

Figure 12:
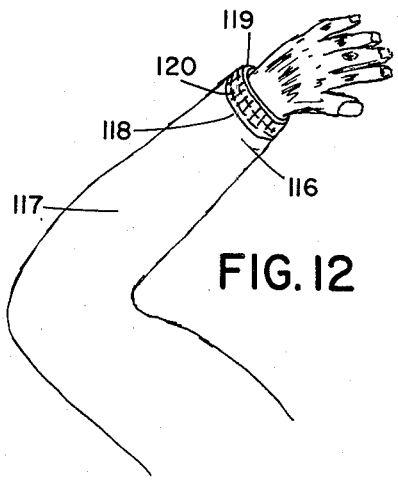
FIG. 12 is a simplified perspective view of a cuff assembly on a sleeve according to the present invention viewed in the configuration it assumes on the wearer.

FIG. 12 illustrates the cuff portion 116 of a garment 117 on the arm of a wearer. The material at the cuff portion is folded over on itself and an elastic member 118 in accordance with the present invention is disposed between the two layers formed by the fold. The longitudinally extending elements of the elastic member have varying cross sectional areas with the element 119 closest the hand having the largest cross sectional area and the element furthest 120 from the hand having the smallest cross-sectional area.

Several different types of materials may be used for disposable apparel, for example, the material may be a non-woven web made of a mixture of fibers consisting predominantly of inexpensive, short, cellulosfc fibers such as short wood pulp fibers or cotton linters in amounts of 75 percent to 98 percent, the balance being textile length fibers such as rayon as described in U.S. Pat. No. 3,663,348 to Liloia, et al.

Non-woven materials suitable for use in disposable apparel such as the forming of dipaers of this invention can have fabric weights in the range of from about 0.5 to 5 ounces per square yard and densities of less than 0.15 g/cc., generally in the range of 0.5 to about 0.1 g/cc. The dry strength of the material for a fabric having a weight of about 1.5 ounces per square yard is at least 0.15 lbs. per inch of width in the machine direction and at least 0.1 lb. per inch of width in the cross direction. Such fabrics have good elongation, loft, softness, and drape characteristics. Materials may also be made of an apertured non woven fabric which is formed, for example, in accordance with the teachings of commonly assigned U.S. Pat. Nos. 2,862,251; 3,081,514; and 3,081,515. Furthermore, materials may also be made from other types of fabric such as those disclosed and described in U.S. Pat. No. 3,485,706 to Evans. Such materials can be made of naturally occurring fibers, synthetic fibers or blends thereof. Typical diaper facings made of polyester type fibers may have a weight of about 0.75 ounces per square yard.

The facing may be the same size as, and coterminous with, the backing; or alternatively, the facing may be wider than the backing and have its side edges inwardly folded so that the facing is coterminous with the backing, as is shown in FIG. 3 of U.S. Pat. No. 3,612,055. In the latter case, the elastic members may be secured above the inwardly folded side edges of the facing. In addition, facings may be made from non apertured materials such as non-woven isotropic webs or apertured polyolefin or polyester films having the desired mositure permeability. In all of the aforementioned facings, the materials should be relatively hydrophobic so as to retard wicking within the facing.

The moisture absorbent batt or panel of a desired shape, but smaller than the facing and backing, can be formed in accordance with the teachings of U.S. Pat. No. 3,612,055 to Mesek, et al.

A suitable backing material for the disposable undergarments embodying the present invention can be an opaque polyolefin; for example, polyethylene about 0.001 inch thick. Another suitable material for this purpose is polyethylene terephthalate having a thickness of about 0.005 inch.

In use, the disposable diaper is applied to the baby by laying out the diaper on a single flat surface and placing the baby thereon. The waist underlying end of the diaper is that end having the fasterner means and the other end of the diaper extends downwardly between the baby's legs. Next, the downwardly extending edge of the diaper is brought up between the baby's legs to a position covering the perineum and contiguous with the front portion of the baby's waist. The diaper thereafter is secured to the baby by placing the corners of the waist portion of the abdomen covering end as far around the baby's waist as they will go and by bringing the corners of the underlying end of the diaper into an overlapping relationship with the aforementioned corners so that the diaper snugly encircles the baby's waist and provides a custom fit. The adhesive tape fasteners are then prepared for use and the diaper is brought in a desired position by simply urging the pressure-sensitive adhesive surface of the tape tap in contact with the adjacent outer surfaces of the opposite corner of the diaper.

In some instances, it may be desirable to have a second fastener available that can be applied just above the thigh of the infant and below the standard fastener to improve and secure the fit of the stretch diaper.

A technique that may be used in the manufacture of the diaper in accordance with the present invention is to apply the adhesive to that portion of the backing or facing layer to which the elastic member is to be secured. In assembling the diaper, pressure is applied to the diaper in the region of the elastic member to adhere the facing and backing together between the apertures in the elastic member.

Broadly, the method of manufacturing the elastic structure of the present invention comprises feeding the novel elastic member in a stretched condition between a pair of web surfaces. One of the web surfaces carries an adhesive. The laminate is pressed together and the web surfaces secured to each other through the apertures in the elastic member. The elastic member is then severed and portions allowed to relax or when a thermoplastic elastic member is used, portions may be heated and rendered inelastic.

It should be pointed out that the term disposable does not always mean a single use product. Though such a definition is correct when referring to diapers, other disposable apparel may be worn a number of times and even in some instances may withstand hand or even machine laundering a number of times.

The foregoing description of the drawings are illustrative and are not to be taken as limiting. Still other variations and modifications are possible without departing from the spirit and scope of the present invention.

I claim:

1. A laminated structure having a gathered marginal area to provide improved fit about a portion of the human body comprising: first and second layers positioned adjacent to one another, said layers being formed of flexible gatherable material, an elastic member disposed between said layers in the marginal area thereof, said elastic member comprising a plurality of interconnected longitudinally extending elastic elements defining apertures therebetween, said elements having different cross sectional areas to provide varying degrees of tension across the width of said marginal area, said first and second layers being secured together through at least some of said apertures.

2. A laminated structure as in claim 1 wherein the first and second layers in the marginal area comprise a single piece of folded material.

3. A laminated structure as in claim 1 wherein the longitudinally extending elastic element adjacent the outermost edge of the marginal area has the greatest degree of tension.

4. A laminated structure as in claim 3 wherein the degree of tension substantially uniformly decreases across the width of the marginal area.

5. A disposable diaper comprising: a moisture-permeable facing layer, an absorbent panel at one side of said facing layer, said absorbent panel being smaller than said facing layer so that marginal portions of the facing layer extend outwardly beyond the edges of said absorbent panel; a moisture-impervious backing layer at the side of said absorbent panel opposite said facing layer, said backing layer being larger than said absorbent panel so that marginal portions of the backing layer extend outwardly beyond the edges of said absorbent panel; means bonding said facing and backing layers to one another; and an elastic member disposed in at least one marginal portion, and affixed therein, said elastic member comprising a plurality of interconnected longitudinally extending elastic elements defining apertures therebetween, said elements having differential cross-sectional areas to provide varying degrees of tension across the width of said marginal portions.

6. A disposable diaper as in claim 5 wherein said elastic member is disposed between said facing layer and said backing layer.

7. A disposable diaper as in claim 6 wherein said facing layer and said backing layer are secured to each other between the longitudinally extending elastic elements of said elastic members.

8. A disposable diaper as in claim 5 wherein the longitudinally extending elastic element adjacent the outermost edge of said marginal portion has the greatest degree of tension.

9. A disposable diaper as in claim 8 wherein the degree of tension substantially uniformly decreases across the width of the marginal portion.

10. A disposable diaper comprising: a moisture-permeable facing layer; an absorbent panel at one side of said facing layer, said absorbent panel being smaller than said facing layer so that side marginal portions of the facing layer extend outwardly beyond the side edges of said absorbent panel; a moisture-impervious backing layer at the side of said absorbent panel opposite said facing layer, said backing layer being larger than said absorbent panel so that side marginal portions of the backing layer extend outwardly beyond the side edges of said absorbent panel; means bonding said facing and backing layers to one another; and an elastic member disposed in each of said side marginal portions, and affixed therein, said elastic members comprising a plurality of interconnected longitudinally extending elastic elements defining apertures therebetween, said elements having different cross-sectional areas to provide varying degrees of tension across the width of said marginal portions.

11. A disposable diaper as in claim 10 wherein the longitudinally extending elastic elements adjacent the outermost edge of each side marginal portion have the greatest degree of tension.

12. A disposable diaper as in claim 11 wherein the degree of tension substantially uniformly decreases across the width of each side marginal portion.

13. A disposable diaper as in claim 12 wherein said elastic members are disposed between said facing layer and said backing layer.

14. A disposable diaper as in claim 13 wherein said facing and backing layers are secured to each other through at least some of said apertures.

15. A disposable diaper comprising: a first outer layer in the form of a moisture-impervious backing; an absorbent panel positioned in superposed relationship with respect to said backing, said panel being smaller than said backing and spaced inwardly from the sides and ends thereof; a second outer layer in the form of a moisture-pervious facing positioned in superposed relationship with respect to said panel, said facing being larger than said panel and having side and end marginal portions thereof secured to said backing; an elastic member disposed in each side margin of the diaper, and affixed therein, said elastic member comprising a plurality of interconnected longitudinally extending gathering elements defining apertures therebetween, said elements having different cross-sectional areas to provide varying degrees of tension across the width of said side marginal portions.

16. A disposable diaper as in claim 15 including a gathering means disposed in at least one end margin of the diaper.

17. A disposable diaper as in claim 16 wherein the longitudinally extending elastic elements adjacent the outermost edge of each side marginal portion have the greatest degree of tension.

18. A disposable diaper as in claim 17 wherein the degree of tension substantially uniformly decreases across the width of each side marginal portion.

19. A disposable diaper as in claim 18 wherein said elastic members are disposed between said facing and said backing layer.

20. A disposable diaper as in claim 19 wherein said facing and backing layers are secured to each other through at least some of said apertures.

21. A disposable diaper as in claim 20 including a gathering means disposed in at least one end margin of the diaper.

22. A disposable diaper as in claim 21 wherein said gathering means comprises a plurality of interconnected gathering elements defining apertures therebetween.

23. A disposable undergarment, suitable for use in training infants or by incontinent children or adults, which comprises a front portion, a rear portion, and a crotch portion connecting said front and rear portions; both said margins of said front portion being joined to respective side margins of said rear portion so as to define a waist portion and leg apertures, said undergarment having a moisture-pervious inner layer adapted to contact the wearer's skin, an outer layer and an intermediate liquid absorbent panel disposed therebetween, and an elastic member disposed between the ends of the inner layer and the outer layer at the rear portion, said elastic member comprising a plurality of interconnected longitudinally extending elastic elements defining apertures therebetween, said elements having different cross-sectional areas to provide varying degrees of tension across the width of said rear portion, said inner layer and said outer layer being secured together through at least some of said apertures.

24. A disposable undergarment as in claim 23 wherein the longitudinally extending elastic element adjacent the outermost edge of said rear portion has the greatest degree of tension.

25. A disposable undergarment as in claim 24 wherein the degree of tension substantially uniformly decreases across the width of the rear portion containing the elastic member.

26. A disposable undergarment as in claim 23 having an elastic member disposed between the ends of said inner layer and said outer layer at the front portion, said elastic member comprising a plurality of interconnected elastic elements defining apertures therebetween, said elements having different cross-sectional areas to provide varying degrees of tension across the width of said front portion, and said inner layer and said outer layer being secured together through at least some of said apertures.

27. A disposable undergarment as in claim 23 wherein said undergarment is also provided with elastic members disposed in the side margins of said crotch portion, each of said elastic members comprising a plurality of interconnected elastic elements defining apertures therebetween, said elements having different cross-sectional areas to provide varying degrees of tension across the width of the side margin, and said inner layer and said outer layer being secured together through at least some of said apertures.

28. A disposable undergarment as in claim 27 wherein the longitudinally extending elastic element adjacent the outermost edge of each side margin has the greatest degree of tension.

29. A disposable undergarment as in claim 27 wherein the degree of tension substantially uniformly decreases across the width of each side margin.

* * * * *